United States Patent
Gammenthaler

Patent Number: 6,026,674
Date of Patent: Feb. 22, 2000

[54] APPARATUS AND METHOD FOR DETERMINING A PERSON'S SOBRIETY

[75] Inventor: Robert Scott Gammenthaler, Princeton, Tex.

[73] Assignee: Smart Start Inc., Irving, Tex.

[21] Appl. No.: 09/136,837

[22] Filed: Aug. 20, 1998

[51] Int. Cl.$^7$ .............. B60K 27/08; G01N 1/22; G08B 23/00; A61B 5/097
[52] U.S. Cl. .............. 73/19.01; 73/23.3; 422/84; 436/132; 436/900; 340/576; 180/272
[58] Field of Search .................. 73/19.01, 23.3; 422/84; 180/272; 128/730, 719; 340/576; 436/132, 900

[56] References Cited

U.S. PATENT DOCUMENTS

| | | | |
|---|---|---|---|
| 3,831,707 | 8/1974 | Takeuchi | 180/99 |
| 4,487,055 | 12/1984 | Wolf | 73/23 |
| 4,592,443 | 6/1986 | Simon | 180/272 |
| 4,697,666 | 10/1987 | Collier et al. | 180/272 |
| 4,707,336 | 11/1987 | Jones | 422/84 |
| 4,736,619 | 4/1988 | Legrand | 73/23 |
| 4,770,026 | 9/1988 | Wolf | 73/23 |
| 4,905,498 | 3/1990 | O'Donnell et al. | 73/23.1 |
| 5,020,628 | 6/1991 | Bigliardi et al. | 180/272 |
| 5,303,575 | 4/1994 | Brown et al. | 73/23.3 |
| 5,426,415 | 6/1995 | Prachar et al. | 340/576 |
| 5,454,375 | 10/1995 | Rothenberg | 128/716 |
| 5,458,853 | 10/1995 | Porter et al. | 422/84 |
| 5,533,513 | 7/1996 | Ueda et al. | 128/719 |
| 5,573,005 | 11/1996 | Ueda et al. | 128/730 |

*Primary Examiner*—Hezron Williams
*Assistant Examiner*—J. David Wiggins
*Attorney, Agent, or Firm*—Richard L. Wynne, Jr.

[57] ABSTRACT

An apparatus and method for determining the concentration of alcohol present in a gaseous mixture wherein an electronic device employing a fuel cell determines the concentration of alcohol present in the gaseous mixture is disclosed. In particular, the device may be used to determine a person's sobriety by determining the alcohol concentration in a breath sample. To determine the alcohol concentration, the device must be able to accurately determine the volume of breath in the breath sample. The device controls the volume of the breath sample by measuring the pressure of the breath flow through the device and, in response to the pressure, electronically controlling a valve diverting a portion of the breath flow into the fuel cell thereby indicating and ensuring that a predefined requisite amount of breath flow has passed thru the fuel cell. One application of the invention is a sobriety interlock for a machine where the machine remains disabled unless the operator is first determined to have an alcohol concentration below a predetermined level.

20 Claims, 4 Drawing Sheets

APPARATUS AND METHOD FOR DETERMINING A PERSON'S SOBRIETY

BACKGROUND OF THE INVENTION

The present invention relates generally to devices and methods for determining the concentration of alcohol in a mixture of gases. More particularly, the invention relates to a device and method for determining the concentration of alcohol in a breath sample for application in sobriety detection systems and sobriety interlock systems for vehicles and other machines.

Various techniques have been employed for calculating a person's blood alcohol concentration by measuring breath samples. In a first method, the alcohol content in a breath sample is measured using a semiconductor sensor commonly referred to as a Taguchi cell. Although this method provides a low cost device, instruments incorporating this method have proved to have poor accuracy.

A second method employs an infrared absorption technique for determining the blood alcohol concentration. This method has proven to have very high accuracy levels. However, the sensor systems incorporating this technique are cost prohibitive for many applications.

A third method employs a fuel cell together with an electronic circuit. This method is described in U.S. Pat. No. 4,487,055. Although this method allows for more accuracy than the first method, the systems employing this method have continued to be relatively expensive. One reason for the high cost associated with the fuel cell techniques is that the method requires that the breath sample be of a determinable volume. Historically, this has been accomplished through the use of positive displacement components such as piston-cylinder or diaphragm mechanisms. The incorporation of such components within an electronic device necessarily increases the costs associated with the device.

The current invention departs from the use of the expensive positive displacement mechanisms while retaining the accuracy provided by the fuel cell. The current invention employs a valve controlled by a computing device such as a microprocessor to regulate the total volume of gas passing through the fuel cell.

SUMMARY OF THE INVENTION

According to the invention, a sobriety detection system obtaining relatively good accuracy at an acceptable cost is disclosed. In one embodiment, the alcohol concentration in a person's breath is determined by passing a breath sample of determinable volume through a fuel cell. The invention obtains a breath sample of determinable volume by electronically controlling a valve permitting breath flow into the fuel cell. A valve controller limits the duration of time the valve is open based upon the pressure of the breath flow. The fuel cell produces a voltage output proportional to the total volume of alcohol in the breath sample. A computing device determines the total volume of alcohol in the sample from the fuel cell voltage output. The computing device adjusts the valve-open time as a function of pressure to obtain a constant-volume breath sample. Therefore, the alcohol concentration is known directly from the fuel cell voltage by applying the appropriate scale factor.

In another embodiment, the invention is employed in a sobriety interlock device to prevent operation of a machine such as a vehicle, unless the operator's breath alcohol concentration is first determined to be below a predefined level. In this embodiment, the machine operator breathes into the interlock device incorporating the invention. The device then determines whether the alcohol concentration in the breath sample is below the acceptable level. If the concentration is acceptable, the interlock permits enablement of the machine ignition or power supply. If the concentration is above the permissible level, the interlock prohibits ignition or operation of the machine.

When used in an interlock device, the invention may incorporate additional elements and features to prevent an intoxicated person from defeating the interlock by introducing a sample from a source other than the operator's breath. The device may include a temperature sensor which will prohibit enablement of the machine unless the breath flow received has an elevated temperature that is within an acceptable range around human body temperature. The device may also incorporate logic within the computing device to prohibit enablement of the machine unless a pressure oscillation within the breath flow is detected. In the proper operation, the operator generates the pressure oscillation by humming while breathing into the device. The device may also enforce minimum and maximum blow-pressure limits to prevent the use of artificial samples and to detect the use of alcohol-removing filter media, such as activated charcoal, by detecting the resultant low pressure caused by pressure drop across the filter.

DETAILED DESCRIPTION OF THE INVENTION

Figure 1:
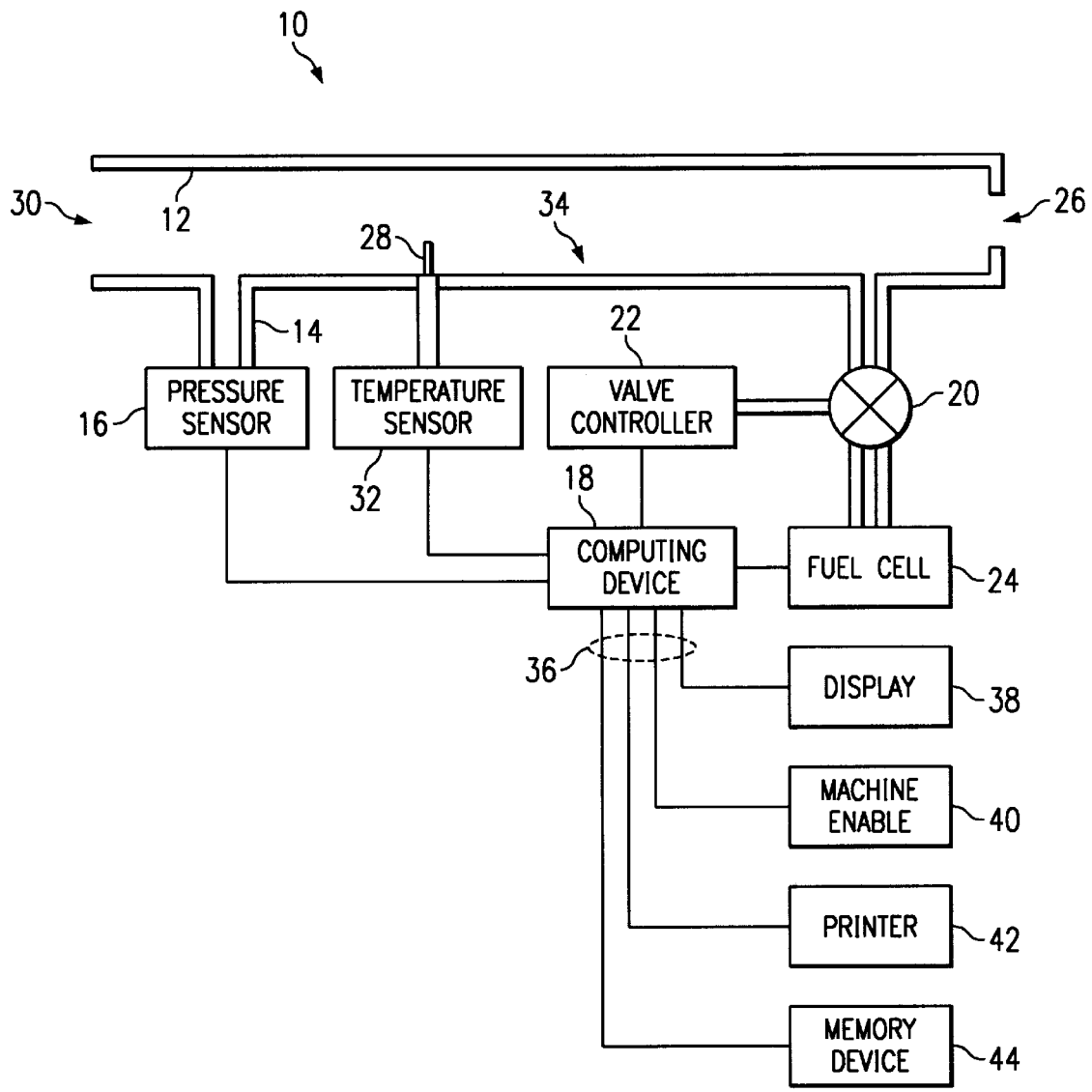
FIG. 1 is a diagrammatic section of a sobriety detection device of this invention with circuitry shown diagrammatically.

Referring to FIG. 1, a sobriety detection system 10 embodying the invention includes a breath induction tube 12 for receiving the breath of the person being tested. The breath induction tube 12 encloses a breath flow channel 34 and includes an inlet 30 and an exit 26. A pressure sensor 16 is connected to the breath induction tube 12 for measurement of the pressure in the breath flow channel 34. Preferably, the pressure sensor 16 is of a resistance-bridge type. The pressure sensor 16 produces an electrical signal proportional to the pressure detected. That signal is input to a computing device 18. Preferably, the computing device 18 is a microprocessor, but it will be appreciated that other devices capable of performing mathematical calculations and generating output signals may be employed. A temperature sensor 32 is also incorporated into the system to measure the temperature within the breath channel 34. The temperature sensor 32, which is preferably of a thermistor type, is electrically connected to computing device 18.

Also connected to the breath induction tube 12 is a fuel cell 24 which is of a type well-known in the art. A valve 20 is positioned between the breath induction tube 12 and the fuel cell 24. When the valve 20 is closed, all of the breath flow exits the breath induction tube 12 through the exit 26. When the valve 20 is open, a portion of the breath flow passes through the valve into the fuel cell 24 while the remainder of the breath flow exits the breath induction tube 12 through the exit 26.

The valve 20 can be of any type suitable for low volume gas flow applications, but preferably is of a needle type with a tapered rubber tip. In the preferred embodiment, when the valve is closed, the tip of the valve 20 seats against a valve seat circumscribing an orifice of approximately 0.015 inches.

Operation of the valve 20 is controlled by a valve controller 22. The valve controller 22 is capable of opening and closing the valve 20 in response to signals from the computing device 18. Preferably, the valve controller 22 is a solenoid electrically connected to the computing device 18.

Figure 2:
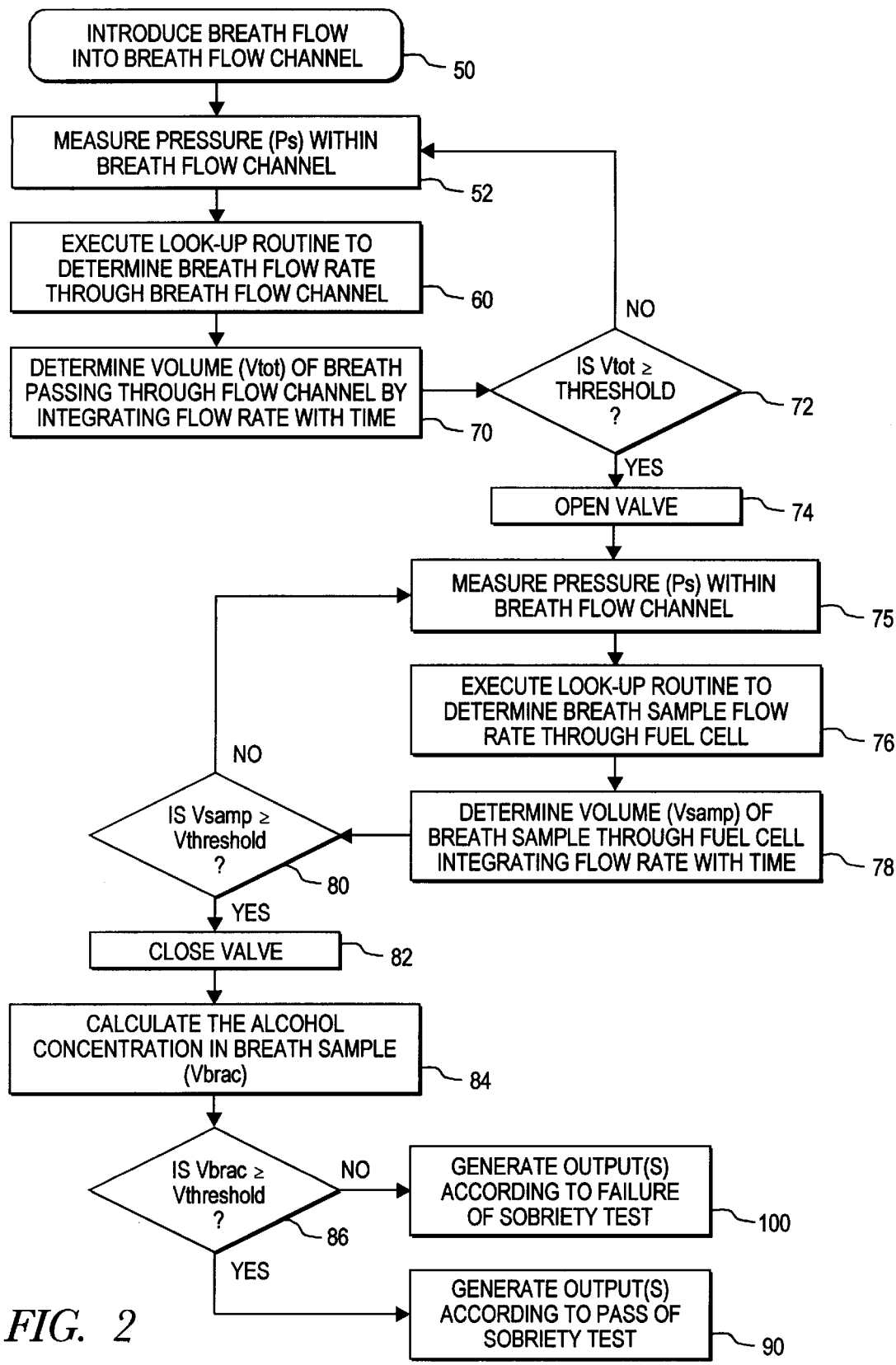
FIG. 2 is a flow diagram illustrating the method of this invention.

FIG. 2 discloses the functional operation of the sobriety detection system 10. As shown at step 50 in FIG. 2, a person's breath is introduced into the breath channel 34. At step 52, the pressure within the breath channel 34 is measured using the pressure sensor 16.

Next, the computing device 18 determines the flow rate of breath through the breath induction tube 12 based on the pressure within the breath channel 34. As depicted at step 60, in the preferred embodiment, the computing device 18 determines an instantaneous flow rate by using a table look-up routine based on empirical data generated for the particular configuration of the device. At the relevant pressure levels, the flow rate through the breath induction tube 12 is approximately proportional to the square root of pressure. At step 70, the computing device 18 calculates the volume of breath that has passed through the breath induction tube 12 by numerically integrating the flow rate over time.

In the preferred embodiment, the valve 20 remains closed for a delay period sufficient for a predefined amount of breath to pass through the breath flow channel 34. Preferably, the valve 20 should remain closed for a time sufficient for at least 1.5 liters of breath to flow through the breath flow channel 34 after the breath flow begins.

Referring to FIG. 2, the decision block 72 requires a determination of whether the requisite amount of breath has passed through the breath induction tube 12 prior to opening the valve 20. If the requisite amount of breath has not passed through the breath induction tube 12, the valve 20 remains closed. But if a sufficient amount of breath has passed through the breath induction tube 12, the computing device 18 transmits a valve open signal to the valve controller 22 to open the valve 20 and to permit a breath sample to flow into the fuel cell 24, as shown at step 74.

Referring to FIG. 1, the fuel cell 24 is electrically connected to the computing device 18. As is well known in the art, the fuel cell 24 produces an electrical signal proportional to the volume of alcohol present in the breath sample. This signal is input to the computing device 18. Referring again to FIG. 2, at step 75, the computing device 18 determines the pressure within the breath flow channel 34 from the output of the pressure sensor 16.

At step 76, the computing device 18 executes a table lookup routine based on the flow pressure measured by the pressure sensor 16 to determine an instantaneous flow rate passing into the fuel cell 24. The breath sample flow rate values within the table lookup routine are based upon empirical data generated for the geometric configuration of the particular device. In the preferred embodiment, the values within the lookup table were developed from experimentation wherein the period of time required to obtain a constant fuel cell output from a flow at a constant pressure was measured. At the relevant pressures, the experimentation confirmed that the breath sample flow rate is approximately proportional to the square root of the pressure. At lower pressures, the actual flow rate departs somewhat from the pressure square root curve because of the presence of a laminar boundary layer. The table lookup routine in the preferred embodiment incorporates adjustments determined from experimentation to correct for the laminar flow.

As shown at step 78 in FIG. 2, the computing device 18 integrates the instantaneous readings of breath sample flow rate over time to calculate the total volume of the breath sample. Decision block 80 requires a determination of whether the breath sample volume has exceeded a predetermined amount. In the preferred embodiment, that predetermined amount is approximately 2 milliliters. If the total volume of the breath sample exceeds the predetermined amount, the computing device 18 transmits a valve close signal to the valve controller 22 to close the valve 20, as represented by step 82.

At step 84 in FIG. 2, after the valve 20 is closed, the computing device 18 calculates the alcohol concentration by dividing the fuel cell signal, representing the total amount of alcohol contained in the breath sample, by the known sample volume calculated from the integration of the instantaneous breath sample flow rate over time. As will be appreciated by those of ordinary skill in the art, the alcohol concentration of "deep-lung" air is approximately proportional to the person's blood alcohol concentration. Thus, the computing device 18 may calculate the person's blood alcohol concentration from the alcohol concentration in the breath sample.

Based on either the blood alcohol concentration or the alcohol concentration in the breath sample, the computing device 18 may generate various outputs depending on the application for the sobriety detection system 10. Because of the approximately-proportional relationship between blood alcohol concentration and the alcohol concentration in the breath sample, it is readily understood that outputs dependent upon predetermined values can be based on either blood alcohol concentration and breath sample alcohol concentration by applying a scale factor to the predetermined values.

As depicted by decision block 86 of FIG. 2, the output may vary depending on whether the alcohol concentration is less than a predetermined level. If the alcohol concentration is less than the predetermined level, the computing device 18 may generate one or more outputs consistent with a "pass" of a sobriety test at step 90. If the alcohol concentration is equal to or more than the predetermined level, the computing device 18 may generate one or more outputs consistent with a "fail" of the sobriety test at step 100. As shown in FIG. 1, the computing device 18 may be connected to various output devices including a display 38, a printer 42, a machine enablement circuit 40, and a memory device 44 through leads 36.

Figure 3:
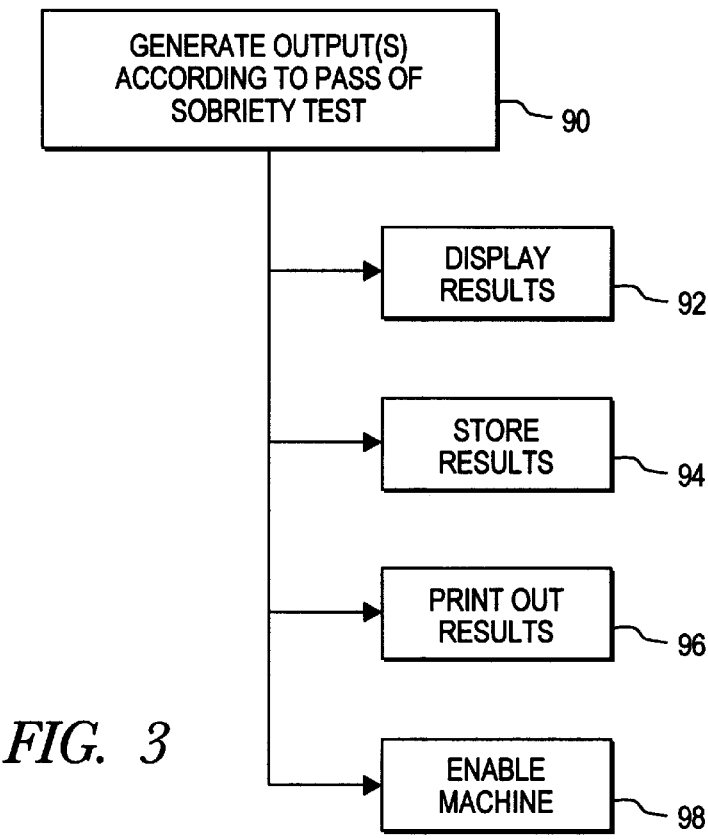
FIG. 3 is a flow diagram illustrating various outputs that may be generated in response to a "pass" test result.

Referring now to FIG. 3, if the blood alcohol concentration is below the predetermined level, the "pass" outputs generated by the computing device 18 may include illumination of an indicator on the display 38 that the sobriety test resulted in a "pass," indication of the numeric value for blood alcohol concentration or another message on the display 38 as shown at step 92, a printout from the printer 42 indicating that the sobriety test resulted in a "pass," and/or a printout of the numeric value for blood alcohol concentration or another printout from the printer 42 as shown at step 96. Likewise, the results of the sobriety test or other information may be stored in a memory device 44 for retrieval at a later time, as shown at step 94.

In a machine interlock device, the computing device 18 may produce an output signal through one of the leads 36 (as shown in FIG. 1) to a machine enablement circuit 40 to permit enablement of the starting system, such as an ignition system, of the machine only if the blood alcohol concentration level is less than or equal to a predetermined amount, as shown at step 98 of FIG. 2.

It is easily appreciated that the interlock device may have application in a wide variety of devices from automobiles and other motorized vehicles, to power equipment and tools, and to industrial or commercial machinery. In fact, the interlock device may be used for relatively simple machines such as electronic locks on doors or mechanical devices. As used herein, the term machine applies to any mechanical device that may rendered inoperative either on signal from the interlock device or unless a signal is received from the interlock device.

Figure 4:
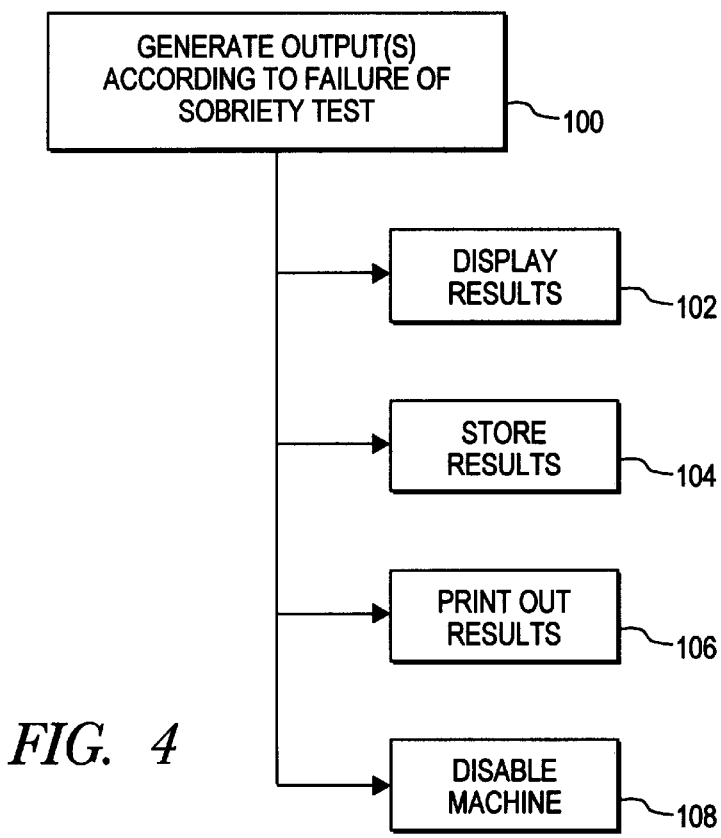
FIG. 4 is a flow diagram illustrating various outputs that may be generated in response to a "failure" test result.

As shown in FIG. 4, if the blood alcohol concentration is greater than or equal to the predetermined level, the "fail" outputs generated by the computing device 18 may include illumination of an indicator on the display 38 that the sobriety test resulted in a "fail," indication of the numeric value for blood alcohol concentration or another message on the display 38, as shown by step 102, a printout from the printer 42 indicating that the sobriety test resulted in a "fail," and/or a printout of the numeric value for blood alcohol concentration or another printout from the printer 42, as depicted by step 106. Likewise, the results of the sobriety test or other information may be stored in a memory device 44 for later retrieval at step 104. The computing device 18 may also generate a signal to disable the operating system of a machine, as shown in step 108.

Figure 5:
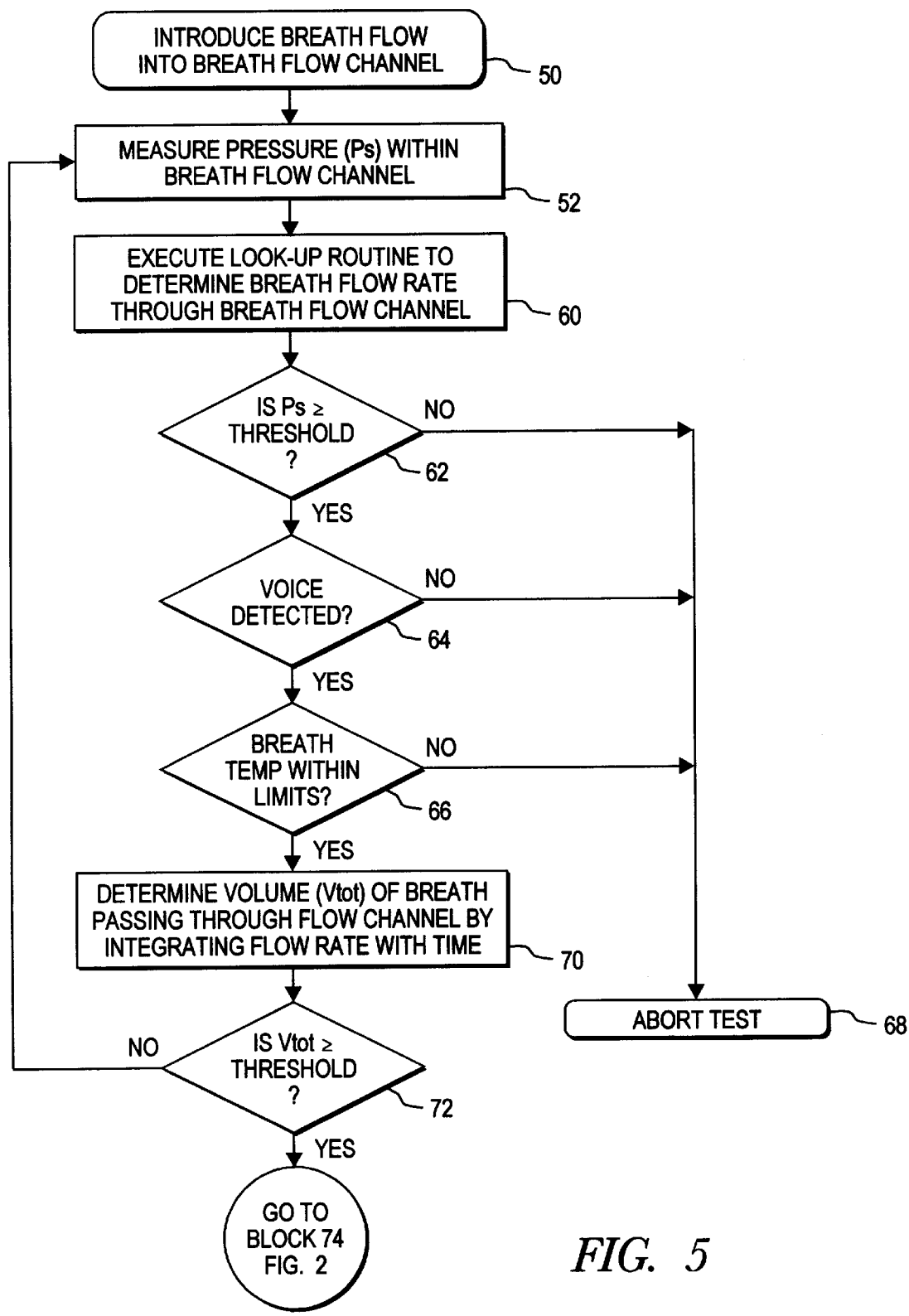
FIG. 5 is a flow diagram illustrating alternative features that may be included within the invention to prevent an intoxicated person from defeating the device to obtain a "pass" test result.

When the sobriety detection system 10 is used in a machine interlock device or any other device where the person using the device may be unsupervised, there is a need to prevent the person being tested from defeating the interlock by introducing air from a source other than the person's breath. FIG. 5 shows an alternative embodiment of the testing process, including features to prevent a person from improperly obtaining a "pass" result. Steps 50, 52, and 60 relate to initiation of the testing process as discussed above in connection with FIG. 2. As shown by decision block 62 in FIG. 5, the sobriety detection system 10 may be configured such that if the pressure in the breath flow tube is below a threshold level, the computing device 18 will cause the test to be aborted. Preferably, the threshold pressure level for performing the sobriety test is approximately 6 inches of water.

In addition or in the alternative, the sobriety detection system 10 may be designed to require the person being tested to hum or make another vocal sound while breathing into the breath induction tube 12. As will be understood by those having ordinary skill in the art, the vocal sound generates a slight pressure oscillation within the breath induction tube 12. As shown by decision block 64 in FIG. 5, the computing device 18 may be configured to abort the test if voice or vocal sound is not detected in a pressure oscillation at the pressure sensor 16.

Referring again to FIG. 1, the sobriety detection system 10 includes the temperature sensor 32 connected to a temperature probe 28 located within the breath channel 34. The temperature sensor 32 measures the temperature of the flow within the breath channel 34 and transmits an electrical signal to the computing device 18 based on the measured temperature. As shown by decision block 66 in FIG. 5, the computing device 18 may be configured to abort the test if the measured temperature does not fall within limits approximating human body temperature. Steps 70 and 72 are described above in connection with the basic operation of the invention in regard to FIG. 2.

It is understood that the actual implementation of the abort test step 68 in FIG. 5 may cause the sobriety detection system 10 to shut down or generate outputs consistent with a "failure" of the test. As applied in a machine interlock device, an aborted test at step 68 will prevent enablement of the machine or disable the machine, depending on the configuration of the machine.

In an additional embodiment, the sobriety detection system 10 may include a heating element. Those skilled in the art will appreciate that the accuracy of the fuel cell 24 is reduced at temperatures below room temperature. Therefore, the heating element may be used to heat the fuel cell 24 when the ambient air temperature is below room temperature.

While the above description constitutes a preferred embodiment of the apparatus and method of the invention, it is to be understood that the invention is not limited thereby and that in light of the present disclosure of the invention, various other alternative embodiments will be apparent to persons skilled in the art. The scope of the present invention is to be limited only by the appended claims.

What is claimed is:

1. An apparatus for measuring the concentration of alcohol in a gaseous mixture, comprising:

(a) a gas induction tube for channeling a flow of the gaseous mixture, the gas induction tube defining a gas flow channel;

(b) a pressure sensor connected to the gas induction tube, the pressure sensor capable of generating an electrical pressure signal in response to the pressure in the gas flow channel;

(c) a fuel cell connected to the gas induction tube, the fuel cell capable of producing an electrical alcohol volume signal proportional to the total volume of alcohol present in a gaseous mixture sample;

(d) a valve disposed between the gas induction tube and the fuel cell, the valve capable of preventing flow between the gas flow channel and the fuel cell;

(e) a computing device electrically connected to the pressure sensor and to the fuel cell, the computing device capable of generating an electrical valve open signal, further capable of determining the alcohol volume in the gaseous mixture sample in response to the electrical alcohol volume signal, further capable of determining a gaseous mixture sample volume in response to the electrical pressure signal, further capable of generating an electrical valve close signal when the gaseous mixture sample volume exceeds a predetermined level ensuring that a predefined requisite volume of gaseous mixture has passed thru the fuel cell, and still further capable of calculating the concentration of alcohol in the gaseous mixture sample from the alcohol volume in the gaseous mixture sample and the gaseous mixture sample volume; and (f) a valve controller connected to the valve and to the computing device, the valve controller capable of opening the valve in response to the electrical valve open signal and capable of closing the valve in response to the electrical valve close signal.

2. The apparatus of claim 1 wherein the gaseous mixture is a person's breath.

3. The apparatus of claim 1 further comprising a temperature sensor connected to the gas induction tube, the temperature sensor electrically connected to the computing device, and the temperature sensor capable of producing an electrical temperature signal proportional to the temperature within the gas induction tube.

4. The apparatus of claim 1 further comprising a heating device connected to the fuel cell.

5. A sobriety interlock for a machine comprising:
  (a) a breath induction tube for channeling a flow of human breath, the breath induction tube defining a breath flow channel, the breath induction tube further defining a breath flow exit;
  (b) a pressure sensor connected to the breath induction tube, the pressure sensor capable of generating an electrical pressure signal in response to the pressure in the breath flow channel;
  (c) a fuel cell connected to the breath induction tube, the fuel cell capable of producing an electrical alcohol volume signal proportional to the total volume of alcohol present in a breath sample;
  (d) a valve having a closed position the valve disposed between the breath induction tube and the fuel cell, the valve capable, when in the closed position, of preventing flow between the breath flow channel and the fuel cell such that the entirety of the flow of breath flows through the breath flow exit;
  (e) a computing device electrically connected to the pressure sensor and to the fuel cell, the computing device capable of generating an electrical valve open signal, further capable of determining the alcohol volume in the breath sample in response to the electrical alcohol volume signal, further capable of determining a breath sample volume in response to the electrical pressure signal, further capable of generating an electrical valve close signal when the breath sample volume exceeds a predetermined level ensuring that a predefined requisite volume of breath flow has passed thru the fuel cell, further capable of calculating the concentration of alcohol in the breath sample from the alcohol volume in the breath sample and the breath sample volume, and still further capable of generating an operations signal;
  (f) a valve controller connected to the valve and to the computing device, the valve controller capable of opening the valve in response to the electrical valve open signal and capable of closing the valve in response to the electrical valve close signal; and
  (g) an electronic circuit connected to the computing device, the electronic circuit capable of controlling the operation system of the machine in response to the operations signal.

6. The sobriety interlock of claim 5 wherein the operations signal comprises a signal generated in response to a determination that the concentration of alcohol in the breath sample is less than a predetermined level.

7. The sobriety interlock of claim 6 wherein the operations signal further comprises a signal generated in response to a determination that the temperature of the breath flow is within a predetermined range.

8. The sobriety interlock of claim 6 wherein the operations signal further comprises a signal generated in response to an oscillation in pressure within the breath induction tube.

9. The sobriety interlock of claim 6 wherein the operations signal further comprises a signal generated only when the electrical pressure signal exceeds a predetermined level.

10. The sobriety interlock of claim 5 wherein the operations signal comprises a signal generated in response to a determination that the concentration of alcohol in the breath sample is greater than a predetermined level.

11. A method of determining the sobriety of a person, comprising the steps of:
  (a) receiving a flow of breath into a breath induction tube;
  (b) determining the pressure of breath flow within the breath induction tube;
  (c) providing a breath flow exit in the breath induction tube for allowing the breath flow to exit the breath induction tube;
  (d) after a portion of the breath flow has exited the breath induction tube, opening a valve disposed between the breath induction tube and a fuel cell to permit a breath sample to flow through the fuel cell;
  (e) generating an electrical alcohol volume signal corresponding to the volume of alcohol in the breath sample detected by the duel cell;
  (f) calculating the volume of alcohol in the breath sample in response to the electrical alcohol volume signal;
  (g) calculating a breath sample volume in response to the pressure in the breath induction tube;
  (h) closing the valve when the breath sample volume exceeds a predetermined level thereby ensuring that a predefined requisite volume of breath flow has passed thru the fuel cell; and
  (i) calculating the alcohol concentration within the person's breath from the volume of alcohol in the breath sample and the breath sample volume.

12. The method of claim 11 further comprising the step of:
  (i) preventing enablement of a machine unless the value of the alcohol concentration in the breath sample is less than a predetermined level.

13. The method of claim 11 further comprising the steps of:
  (i) determining a value for the person's blood alcohol concentration based upon the alcohol concentration of the breath sample; and
  (j) generating an output in response to the person's blood alcohol concentration.

14. The method of claim 13 wherein the step of generating an output comprises sending an enabling signal to a machine only if the person's blood alcohol concentration is less than a predetermined level.

15. The method of claim 13 wherein the step of generating an output comprises displaying a numeric value of the blood alcohol concentration on a display screen.

16. The method of claim 13 wherein the step of generating an output comprises generating one response if the blood alcohol concentration is less than a predetermined level and generating a different response if the blood alcohol concentration is greater than or equal to the predetermined level.

17. The method of claim 13 wherein the step of generating an output comprises printing a message or data on a paper medium.

18. The method of claim 13 wherein the step of generating an output comprises illuminating a pass indicator light in response to a determination that the value for the person's blood alcohol concentration is below a predetermined level.

19. The method of claim 13 wherein the step of generating an output comprises storing the blood alcohol concentration in a storage device.

20. The method of claim 11 further comprising the step of:
  (i) disabling a machine unless the value of the alcohol concentration in the breath sample is less than a predetermined level.

* * * * *